United States Patent [19]

Shaw

[11] Patent Number: 5,576,214

[45] Date of Patent: Nov. 19, 1996

[54] METHOD OF SUPPLYING DISPOSABLE TIPS TO AN ASPIRATOR

[75] Inventor: James D. Shaw, Hilton, N.Y.

[73] Assignee: Johnson & Johnson Clinical Diagnostics, Inc., Rochester, N.Y.

[21] Appl. No.: 306,276

[22] Filed: Sep. 14, 1994

[51] Int. Cl.$^6$ .................................................. G01N 37/00
[52] U.S. Cl. ..................... 436/43; 436/49; 422/63; 422/65; 422/100; 422/103; 422/104; 73/864.01; 73/864.24; 73/864.85; 220/23.4
[58] Field of Search .................. 436/43, 48, 49, 436/174, 180, 183, 809; 422/100, 99, 103, 104, 63, 65; 220/23.2, 23.4; 221/30, 32; 222/80; 73/864.85, 864.01, 864.11, 864.14, 864.21, 864.24; 156/290, 308.2, 308.4

[56] References Cited

U.S. PATENT DOCUMENTS

| | | | |
|---|---|---|---|
| 3,302,854 | 2/1967 | Midgley et al. | 220/23.4 X |
| 4,154,795 | 5/1979 | Thorne | 422/99 |
| 4,215,092 | 7/1980 | Suovaniemi et al. | 422/100 |
| 4,472,357 | 9/1984 | Levy et al. | 422/102 |
| 4,565,100 | 1/1986 | Malinoff | 73/863.32 |
| 4,731,225 | 3/1988 | Wakatake | 422/65 |
| 4,892,006 | 5/1989 | Smith et al. | 74/552 |
| 5,000,921 | 3/1991 | Hanaway et al. | 422/100 |
| 5,054,631 | 10/1991 | Robbins, III | 215/1 A |
| 5,096,672 | 3/1992 | Tervamäki et al. | 422/102 |
| 5,232,669 | 8/1993 | Pardinas | 422/100 |
| 5,240,679 | 8/1993 | Stettler | 422/67 |
| 5,392,914 | 2/1995 | Lemieux et al. | 206/499 |
| 5,409,127 | 4/1995 | Stratford et al. | 220/23.4 |

FOREIGN PATENT DOCUMENTS

| | | |
|---|---|---|
| 478905A1 | 4/1992 | European Pat. Off. . |
| 547710A3 | 6/1993 | European Pat. Off. . |

Primary Examiner—Long V. Le
Attorney, Agent, or Firm—Dana M. Schmidt

[57] ABSTRACT

An array of tips is disclosed for multiple loading onto plural aspirators, wherein the array comprises columns of tips temporarily joined together within and between columns, at discontinuously spaced junctions. The array is moved along in tracks spaced so as to diverge when tip columns are to be broken out of the array. Each track ends in a step-down ledge that allows an aspirator to punch an engaged tip out of its column.

3 Claims, 3 Drawing Sheets

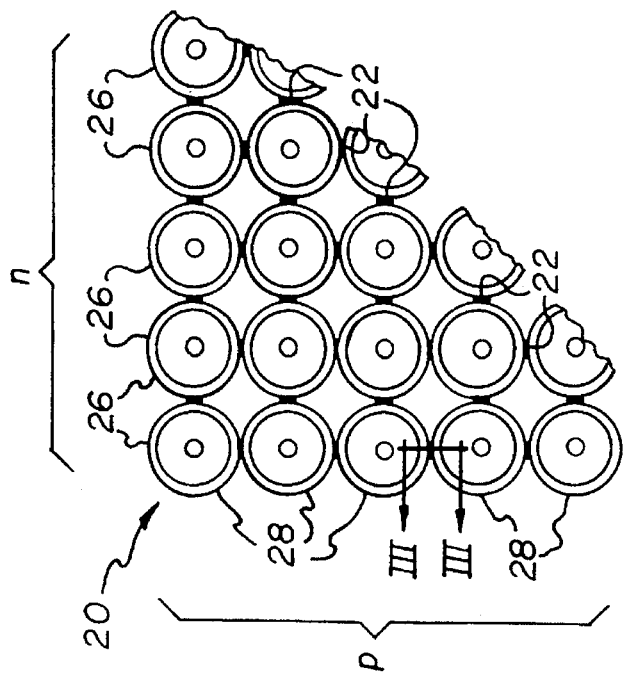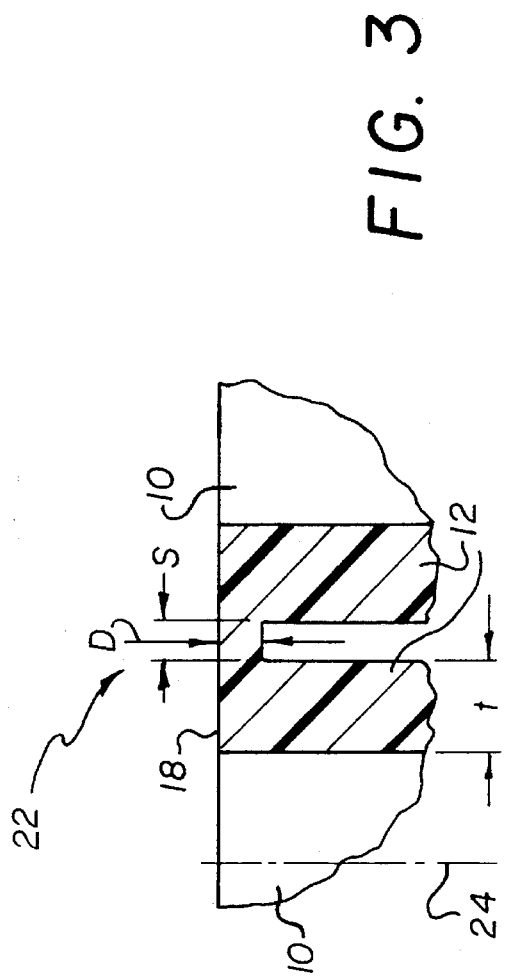

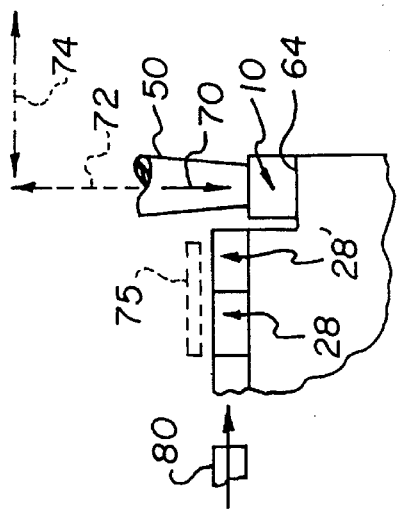
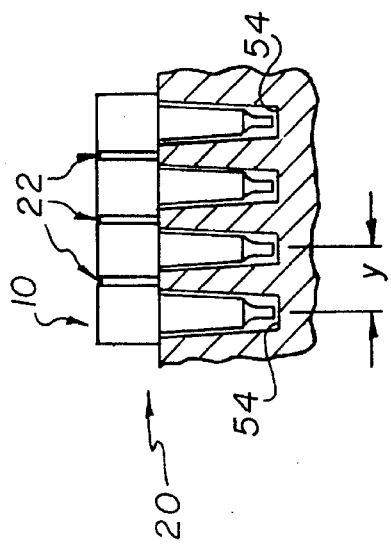
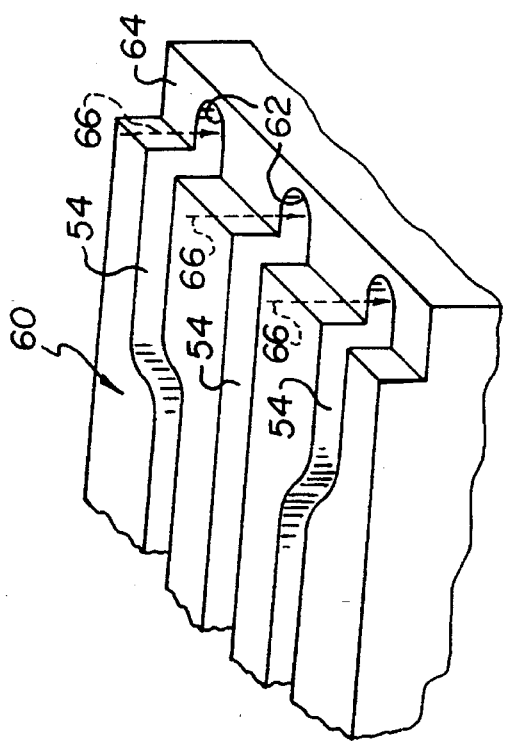

METHOD OF SUPPLYING DISPOSABLE TIPS TO AN ASPIRATOR

FIELD OF THE INVENTION

This invention relates to a temporary array of disposable tips and to apparatus and the manner in which that is used to supply such tips to an aspirator.

BACKGROUND OF THE INVENTION

In the field of chemical analyzers, there is a need to enhance the throughput, particularly at large user sites such as large hospitals. When using dried slides as the test elements, for example, the "Electachem"® slides available from the Clinical Diagnostics Division of Eastman Kodak Company, a limiting factor in increasing the throughput is the speed at which the aspirator can aspirate and dispense patient sample onto the slide test elements. This speed in turn is affected by the need for the aspirator to repeatedly eject the disposable tip previously used, and pick up a new one, each time a different patient sample is to be tested. Such a mechanical operation is time consuming.

One solution to the time needed to eject and pick up a new disposable tip is to use more than one aspirator at the metering station. However, one of the difficulties in doing this is that multiple aspirators require a multiple of supplies of tips. No arrangement has been available for tripling or quadrupling the supply for a triplet or quartet aspirator, without unduly burdening operators with an impossible task of manual loading thousand of tips per hour in an ordered array.

An alternative is to supply tips in a rack that is sampled automatically. This solves the problem of operator labor but adds significant cost to the tips. In addition, the rack then must be disposed, adding to the laboratory cost of waste management as well as negatively impacting the environment.

Hence, prior to this invention there has been a need for a mechanism and method that will somehow supply an array of tips to a multiple aspirator system in an analyzer, without requiring separate hand-placement of each and every tip in the array and without requiring the disposal of empty tip racks.

SUMMARY OF THE INVENTION

I have devised an array of disposable tips and apparatus and method which solve the aforesaid need.

More specifically, in accordance with one aspect of the invention, there is provided an array of disposable tips for use with an aspirator, each of the tips having an aspirator-mounting end and an end opposite thereto that is apertured for liquid ingress and egress, the array comprising a plurality of rows and a plurality of columns of the tips, the rows and columns being separably joined together at temporary junctions located adjacent to the aspirator-mounting end at discrete points discontinuously spaced around the periphery of the tips to permit ready breakage of the junctions on demand.

In accordance with another aspect of the invention, there is provided apparatus for feeding disposable tips to an aspirator on which the tips are individually mounted one at a time, from a bulk source, the apparatus comprising a plurality of n tracks for feeding n columns of the tips separably joined together at one end thereof so that all tips in a column are temporarily attached at junctions, and all the columns are temporarily attached at junctions, the tracks being converged together at one end thereof to hold and feed the columns without breaking the junctions between columns, the tracks thereafter diverging towards an end opposite to the one end so as to break apart the junctions between the columns but not within the columns, and means for severing individual tips from each of the columns at a location in the tracks after the tracks have diverged.

In accordance with yet another embodiment of the invention, there is provided a method of supplying disposable tips to an aspirator, each tip having an aspirator engaging end and a liquid ingress end, comprising the steps of a) assembling them in at least one column with the aspirator-engaging ends all adjacent;

b) joining the column of tips together in a temporary array by forming discontinuous junctions spaced around the periphery of each of the tips adjacent to the aspirator-engaging end;

c) supplying the column array to an aspirator; and d) severing a tip one at a time from the column.

Accordingly, it is an advantageous feature of the invention that an array of tips is easily manually positioned in apparatus feeding to an aspirator, such that an entire temporary bulk of a two-dimensional array of columns and rows of the tips is mounted all at once, the apparatus thereafter automatically breaking the bulk into individual tips for use in aspiration.

Other advantageous features will become apparent upon reference to the following "Detailed Description" when read in light of the attached drawings.

BRIEF DESCRIPTION OF THE DRAWINGS

FIG. 1 is a partially broken-away isometric view of an array of tips temporarily joined together in accordance with the invention;

FIG. 2 is a fragmentary plan view of the array;

FIG. 3 is an enlarged, fragmentary section view taken along line III—III of FIG. 2;

FIG. 5 is a fragmentary section view taken along line V—V of FIG. 4, with the tip array show in full;

FIG. 6 is a fragmentary isometric view of the track mechanism of FIGS. 4 and 5, showing more clearly the one end of the track apparatus; and FIG. 7 is a fragmentary side elevational view of the track end of FIG. 6, with tips present, illustrating the separation of individual tips from each column of tips.

DETAILED DESCRIPTION OF THE INVENTION

Figure 4:
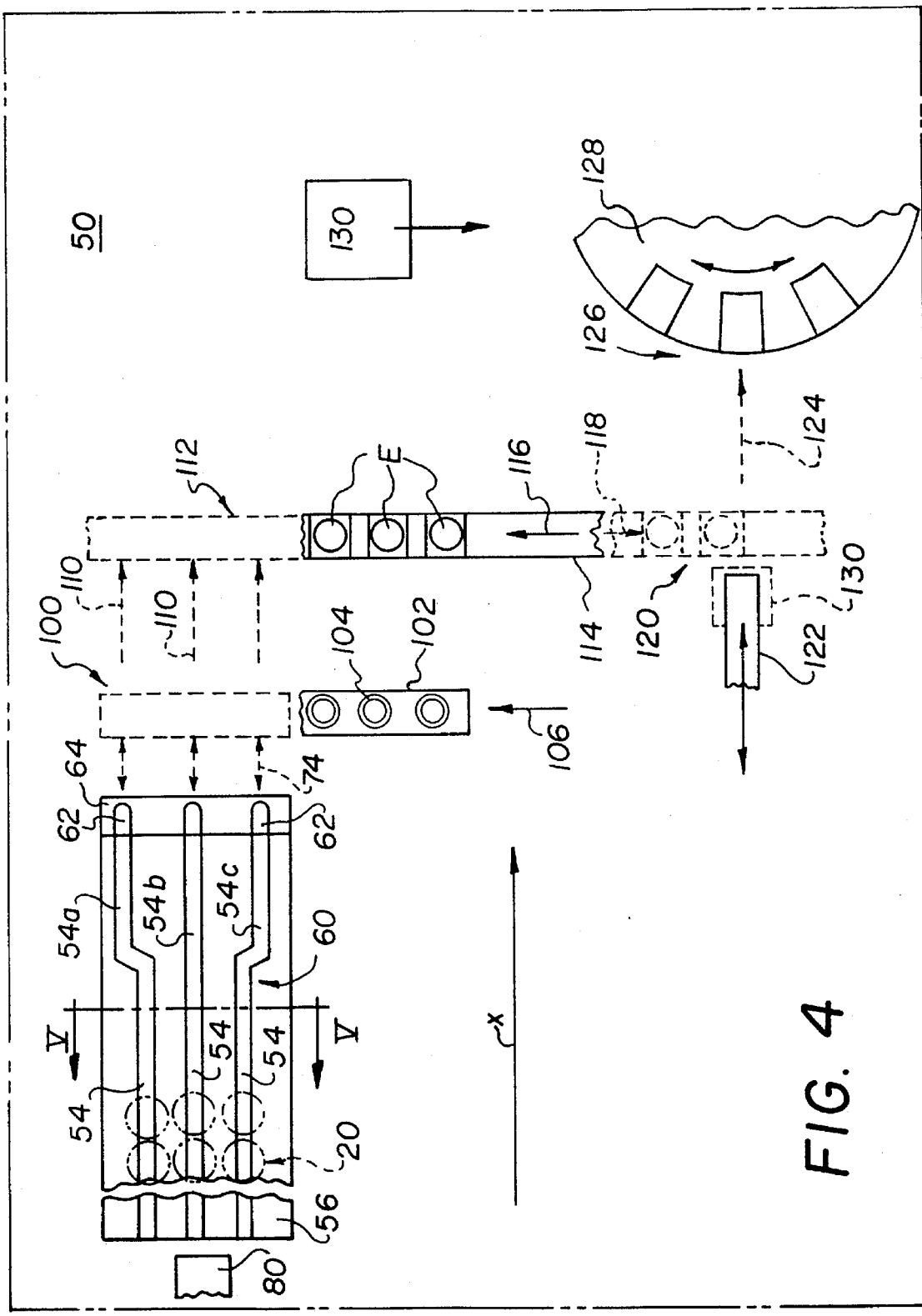
FIG. 4 is a partially schematic diagram in plan, of an analyzer and the apparatus of the invention used with the tip array of the invention, the array appearing only in phantom.

The following is a description of the invention in its preferred embodiments, in which the disposable tips have a preferred configuration especially at the aspirator-engaging end; are temporarily joined together at the extreme end of said aspirator-engaging end; are in an array, when used, that is only n columns wide where n is a preferred integer; and is used with a sample and slide conveyance system of a particular type. In addition, the invention is useful regardless of the exact shape of the aspirator-engaging end or where at such ends the temporary junctions are made, regardless of the number of columns used, and regardless of the rest of the analyzer used to convey and test samples and slides used with the aspirator. Indeed, the invention does not need to be in an analyzer.

Hence, the tips 10 used, FIG. 1, with the invention are those conventionally available under the trademark "Ektachem" tips from the Clinical Diagnostics Division of Eastman Kodak Company. Such tips have a larger end that features a cylindrical shoulder 12 used to temporarily engage an aspirator, and a smaller end featuring a liquid ingress and egress aperture 14, as is well-known. Shoulder 12 preferably projects outwardly away from the body 16 joining shoulder 12 to aperture 14, but this is not essential. Shoulder 12 has a top surface 18 at the extreme end.

In accordance with one aspect of the invention, these otherwise conventional tips are temporarily and separably joined together in a two-dimensional array 20, by reason of temporary junction 22 formed at discrete locations discontinuously spaced around the periphery of shoulder 12. Hence, junctions 22 are adjacent to the aspirator-mounting end. Most preferably, they are at the extreme top surface 18, extending downwardly a short distance D, FIG. 3, parallel to the axis 24 of each tip 10. (The dimensions of junction 22 in FIG. 3 are exaggerated for clarity.)

The preferred dimensions for distance D and the spacing apart of tips 10 by distance S, as well as the use of discontinuous spacing of the junctions around the periphery of each tip, are selected to allow easy severance of each tip from the array as needed. On the other hand, such a two-dimensional array is inherently strong enough at junctions 22 to allow an operator to pick up an array 20, FIG. 2, that has n number of columns 26 with p number of rows 28 in those columns. As shown in FIG. 2, n is 6 and p is 6, but any integers can be used.

As is apparent for such an array, there are 2, 3 or at most 4 such temporary junctions on each tip, joining it with 2, 3 or 4, respectively, neighboring tips.

For specific examples, each junction 22, FIG. 3, is such that the spacing S between tips is no larger than about 0.13 mm (5 mils), and distance D is about 0.25 mm (with a depth into the page of drawings, not shown, of about the same—0.25 mm). By comparison, thickness t of shoulder 12 is about 1 mm. Such dimensions for junction 22 are selected to ensure it can be readily automatically broken as described hereafter during the tip processing in the analyzer, and at the same time allow the tips to be easily assembled in such an array as a bulk object.

Such junctions 22 are preferably formed by hot-welding the tips at surface 18 to melt the polypropylene plastic comprising the tips, just at junctions 22. If spacing S were larger than the 0.13 mm value, the weld becomes more difficult to achieve without substantially deforming surface 18, e.g., without depressing it and thus deforming shoulder 14 and its engagement with the aspirator. Furthermore, any junction that bridges the gap with a substantial value of S creates a more difficult junction for subsequent breakage.

Alternatively, a suitable adhesive can be used at junctions 22 to temporarily join the tips together. The amount and type of adhesive is selected to allow breakage of the junctions to easily occur in the manner described hereinafter.

Thus, the method of assembling the array is to preferably position the tips in columns 26 and joining each tip within a column by hot-welding at the junctions. Most preferably, at the same time each column 26 is temporarily joined to its adjacent columns by hot-welding in the perpendicular direction as well, completing the two-dimensional array.

Thereafter, the array 20 is supplied to the aspirator 52 of an analyzer 50, FIG. 4, preferably by mounting it in plural tracks 54 that start out from end 56 parallel and spaced apart a distance "y", FIG. 5, that is approximately equal to spacing between adjacent columns 26 in the array. Such a spacing keeps the columns joined together at their junctions 22. However, as tracks 54 extend away from end 56, they reach a point 60 where they diverge apart a distance sufficient to break apart columns one from the other, without breaking the junctions within each column. Hence, the radius of bending at 60 is large enough (e.g., about 10 cm) to maintain the junctions 22 within the columns.

To allow individual tips to be broken off their respective columns, each track 54 terminates at ends 62 in a step-down ledge 64, FIG. 6, constructed so that aspirator 50, FIG. 7, when pushed down in the direction of arrows 66, FIG. 6, into a tip hanging out over ledge 64, will break off the tip, FIG. 7, and move it down to the ledge 64, arrow 70. Thereafter, aspirator 50 picks up the tip, arrow 7E, and moves it to the rest of the analyzer, arrow 74.

Alternatively, a mandrel, not shown, could be mounted under the position of ledge 64 in place of the ledge, to move into engagement with a tip hanging out at track end 62, and to raise it away from its column into contact with raised aspirator 50, thus breaking the tip's junction with its column. However, in that case a clamp 75, shown in phantom, FIG. 7, would be used to hold the rest of the column in place, e.g., rows 28 and 28.

It will be appreciated that one, two or three aspirators 50 (only one being shown in FIG. 7) can be used to pick up a tip at ends 62 of the three tracks 54. If three are used, each aspirator reciprocates back and forth, arrow 74, FIG. 4. If the number of aspirators is less than the number of tracks, it preferably also moves between tracks to get a tip from an adjacent track, as needed.

Movement of an array 20 and the severed columns along tracks 54 is achieved by any suitable means such as a pusher rod 80, FIGS. 4 and 7, that pushes on the distal end of the array. In such an arrangement, a row 28 of tips is not advanced out over ledge 64 until all of the previous row 28 has been deleted for all of the tracks.

Thus, rows 28 of the array are confined to a first, preferably horizontal, plane when at the position shown for row 28', FIG. 7, and even when advanced to suspend out over ledge 64 before aspirator 50 makes contact. However, upon contact between aspirator 50 and a suspended tip, the tip 10 is pushed down to the plane of ledge 64, which is below the plane of row 28'.

As shown the plane of the array of tips while still temporarily joined, e.g., when at the position of row 28', is shown as being a constant horizontal plane. However, the guiding surface need not be maintained in one plane but can depart therefrom, as long as the departure is along gradual bends that are insufficient to break the junctions 22 between tips. Such bending out of a single plane is easier to achieve after point 60 is reached in track 54, FIG. 6, as prior to that the junction of all the columns together tends to inhibit the array from moving out of its initial plane of support.

It will be appreciated that track 54a, FIG. 4, need not divert from track 54b at the same point along dimension "x" that track 54c diverts.

Once aspirator 50 has a tip 10 mounted thereon, it can be moved to the rest of the analyzer 50, FIG. 4. The construction of the remaining analyzer will depend on what tests are to be run and with what throughput. As will be readily apparent to one skilled, a variety of analyzer constructions is possible from that point on, and such does not constitute part of this invention. By way of example, however, the 1, 2 or 3 aspirators 50 preferably move, arrow 74, to an aspirate station 100 into which a tray 102 of tubes 104 bearing patient sample liquid is pushed, arrow 106, such tray for example being one of those described in U.S. Pat. No. 5,008,082. The aspirator is then lowered into one of the tubes 104, and aspirates some liquid into the tip. It is then raised and moved further, arrows 110, to a dispense station 112. A plurality of slide test elements is then conveyed, arrow 116, into station 112, for example, 3 such elements E spaced apart on a pusher blade 114. The aspirator(s) are lowered into position above elements E and liquid is dispensed onto them. Blade 114 is then withdrawn, arrow 118, to a transfer station 120 at which another pusher blade 122 is used to push a now-wetted element E off blade 114, arrow 124, into an incubator 126 which can feature a rotating rotor 128. The same blade 122 can be used to "deal" a test element off the top, or bottom, of a cartridge 130 of test elements.

Reading of the test elements after incubation is done using a conventional detector 130, which can be, e.g., a reflectometer, located to one side or underneath rotor 128.

Because n number of test elements E are simultaneously metered with sample from n number of pipette tips, as a maximum, provided from n columns in array 20, the throughput of analyzer 50 is not slowed down by the aspirate-and-dispense operations. (As shown in FIG. 4, n=3).

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

I claim:

1. A method of supplying disposable tips to an aspirator, each tip having an aspirator-engaging end and a liquid ingress end, comprising the steps of:

a) assembling the tips in at least one column with the aspirator-engaging ends all adjacent;

b) joining said column of tips together in a temporary array by forming discontinuous junctions spaced around the periphery of each of said tips adjacent to said aspirator-engaging end, by hot-welding said aspirator-engaging end of each tip to an adjacent tip in said column;

c) joining said at least one column to a second column of tips formed substantially identically to said at least one column, by forming discontinuous junctions spaced around the periphery of each of said tips of adjacent columns at locations adjacent to said aspirator-engaging end;

d) supplying said temporary column array to an aspirator;

e) severing each of said columns from said array while maintaining the junctions between tips in each column wherein said steps d) and e) comprise mounting said array in a plurality of tracks, each column to a track, said tracks having a distance spacing them apart that is approximately equal to the spacing apart of said columns while joined in the array; and said severing step comprises moving said array to a continuance of said tracks wherein said spacing apart of said tracks is greater than the spacing apart of said columns, so that junctions between columns, but not within columns, are broken; and f) severing a tip one at a time from said column.

2. A method as defined in claim 1, wherein said step f) comprises severing a tip one at a time from said column by pushing an aspirator into a first tip and through an end of said tip column so as to push said first tip out of the plane of said column, breaking said junction.

3. A method as defined in claim 1, wherein said joining of columns comprises the step of hot-welding said aspirator-engaging end of each tip to a tip of an adjacent column.

* * * * *